United States Patent [19]
Cassel

[11] Patent Number: 5,823,363
[45] Date of Patent: Oct. 20, 1998

[54] MEDICAL SYRINGE HOLDING/TRANSPORT APPARATUS

[76] Inventor: Douglas Cassel, 1766 Port Manleigh Cir., Newport Beach, Calif. 92660-6622

[21] Appl. No.: 733,439

[22] Filed: Oct. 18, 1996

[51] Int. Cl.⁶ ........................................................ A47F 7/00
[52] U.S. Cl. .............................. 211/60.1; 211/74; 206/366
[58] Field of Search ............................... 211/60.1, 69, 74, 211/85.13; 206/571, 366, 365, 364, 369, 370

[56] References Cited

U.S. PATENT DOCUMENTS

| | | | |
|---|---|---|---|
| 3,261,660 | 7/1966 | Wilkinson | 211/60.1 X |
| 4,383,615 | 5/1983 | Aquino | 211/60.1 |
| 4,397,395 | 8/1983 | McKelvey | 206/369 X |
| 4,850,484 | 7/1989 | Denman | 211/74 X |
| 5,099,992 | 3/1992 | Heimreid | 206/366 |
| 5,190,169 | 3/1993 | Sincock | 211/60.1 |
| 5,372,252 | 12/1994 | Alexander | 206/366 X |

*Primary Examiner*—Robert W. Gibson, Jr.
*Attorney, Agent, or Firm*—Sereboff & Buyan, LLP

[57] ABSTRACT

An article of manufacture which is constructed to receive and hold a plurality of syringes of differing size. The article comprises a substantially rigid frame having a plurality of syringe-receiving cavities formed therein. Each of the syringe-receiving cavities is sized and configured to receive and hold a syringe in a generally vertical orientation. At least some of the syringe-receiving cavities comprise variable diameter syringe-receiving cavities which are adapted to receive different sizes of syringes.

10 Claims, 3 Drawing Sheets

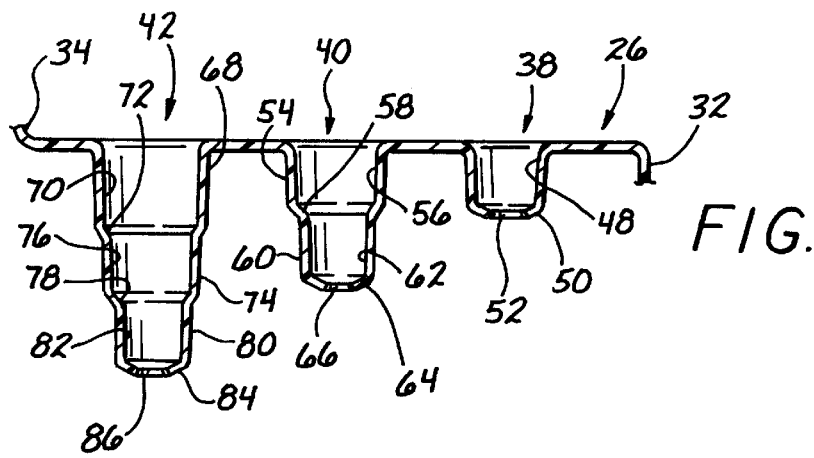
FIG. 3
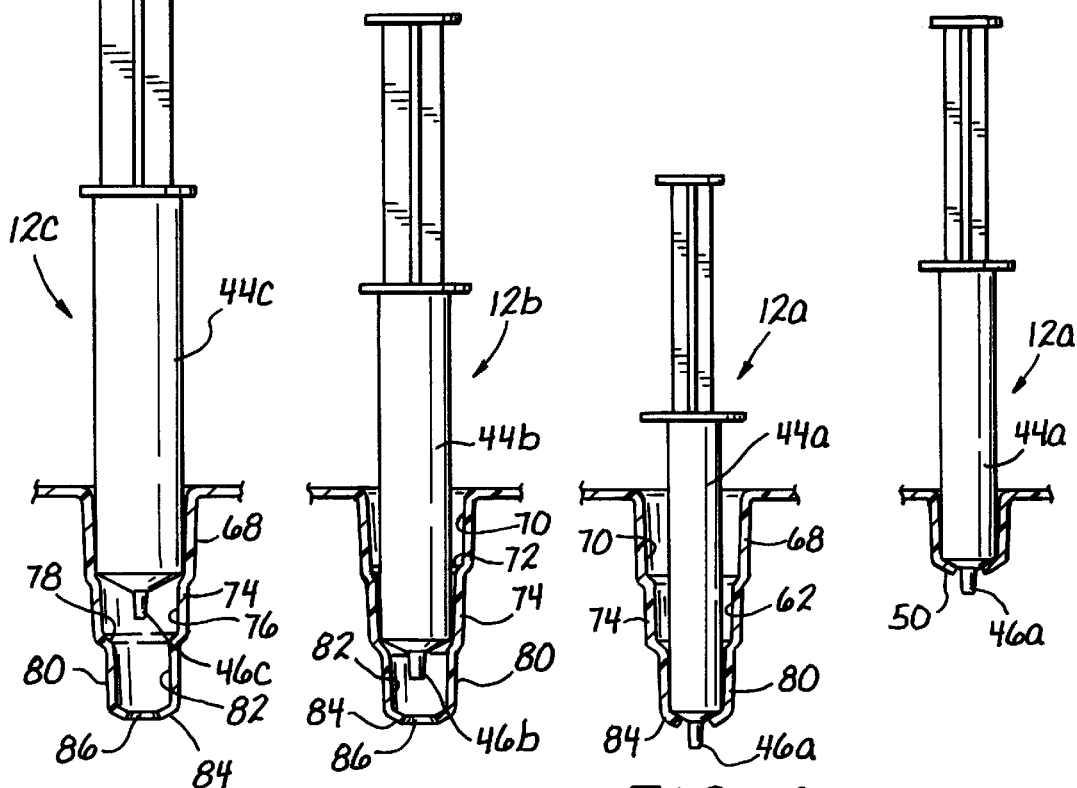
FIG. 4a
FIG. 4b
FIG. 4d
FIG. 4c

MEDICAL SYRINGE HOLDING/TRANSPORT APPARATUS

FIELD OF THE INVENTION

The present invention pertains generally to medical devices, and more particularly to an apparatus which is designed and constructed to hold a plurality of pre-filled syringes of differing size.

BACKGROUND OF THE INVENTION

Many types of medical and surgical procedures require the use of syringes which have been filled with one or more injectable agents such as radiographic contrast media, drugs, fluids, solutions, vaccines, etc.

In particular, many radiographic imaging procedures (e.g., angiographies, CT scans, angioplasty, coronary procedures, clot lysis, transjugular shunt placement, dilatations, endourology procedures, biliary procedures) require the repeated injection of a radiographic contrast medium (e.g., dye) into a patient. Such repeated injections of radiographic contrast media are typically performed using a plurality of hypodermic syringes which have been pre-filled with the desired amount(s) of the desired contrast agent(s). In order to avoid over-dosing the patient with the radiographic contrast agent or medium, it is desirable to minimize the volume and/or concentration of each injection. Thus, in many procedures, it is common practice to have a substantial number of syringes of different size which may be filled with different volume(s) or different concentration(s) of the contrast medium, in order to allow the angiographer to administer various different concentration(s) and/or volume(s) of the contrast medium at different times.

It is heretofore been common practice for a bottle or bag of radiographic contrast solution to be prepared and placed at the patient's procedure table prior to the procedure, to allow the angiographer or assistant to individually fill and/or dilute each syringe immediately prior to use, using the large bottle or bag of the radiographic contrast solution. Such intermittent filling of syringes necessarily requires the angiographer to divert his/her attention from the procedure, or to utilize the help of a technician or other trained individual who can intermittently fill and prepare the required syringes.

As previously indicated, common practice has been to utilize a prepared vial or bag of the contrast solution at the patient's procedure table during the radiographic procedure. Any left over contrast solution in that vial or bag is typically discarded since established infection control practices prevent such solution from being utilized for patients other than the one at whose procedure table the vial or bag has been located.

Given the present-day motivation to decrease and contain healthcare related costs, it is desirable to develop new methods and apparatus for minimizing the cost of medical procedures. In particular, the cost of many angiographic imaging procedures may be minimized by a) eliminating the number of personnel (e.g., technicians) required to be present for a given procedure, and b) eliminating waste of unused radiographic contrast solutions by enabling such solutions to be used for multiple patients without compromising or violating sound infection control practices.

Accordingly, there exists a need in the art for an apparatus (e.g., a rack) which will receive and hold various sizes of medical syringes which have been prefilled with material (e.g., radiographic contrast solution) at a central location, and which may subsequently be transported from such central location, by the apparatus, to a procedure-room for subsequent use at the patient's procedure table during a medical procedure.

SUMMARY OF THE INVENTION

In accordance with the present invention, there is provided an article of manufacture (i.e., a tray) which is constructed to receive and hold a plurality of syringes of differing size. The tray comprises a substantially rigid frame which includes a plurality of sidewalls having top and bottom edges. The top edges of at least some of the sidewalls are of a stepped configuration, with at least one upper wall being mounted upon the top edges of the sidewalls. In this respect, the upper wall defines a tier which is preferably rectangularly configured and defines a generally planar top surface. In the preferred embodiment of the present invention, the frame includes a first, upper tier, a second, middle tier, and a third, lower tier which are disposed at different heights or elevations relative to each other.

Formed within the top surfaces of the first and second tiers are a plurality of syringe-receiving cavities, each of which is sized and configured to receive and hold a syringe in a generally vertical orientation. At least some of the syringe-receiving cavities are variable diameter syringe-receiving cavities which are adapted to receive different size of syringes. More particularly, the syringe-receiving cavities formed in the first and second tiers comprise first size cavities for receiving and holding a first size syringe. In addition to the first size cavities, the first and second tiers each include second size cavities for receiving and holding either a the first size syringe or a second size syringe, as well as third size cavities for receiving and holding either the first size syringe, the second size syringe, or a third size syringe.

In the preferred embodiment, each first size cavity defines inner and bottom walls for supporting the cylindrically configured, tubular body of the first size syringe. In this respect, the inner wall of the first size cavity is of a first diameter which is substantially equal to but slightly exceeds the outer diameter of the body of the first size syringe. The bottom wall of the first size cavity includes an aperture disposed therein for receiving the distal tip of the body of the first size syringe.

Each second size cavity itself defines a first, top region having an inner wall and an annular shoulder for supporting the body of the second size syringe. The inner wall of the second size cavity is of a second diameter which is substantially equal to but slightly exceeds the outer diameter of the body of the second size syringe. In addition to the first region, each second size cavity defines a second, bottom region having inner and bottom walls for supporting the body of the first size syringe. In this respect, the inner wall of the second region of the second size cavity is of the first diameter which is substantially equal to but slightly exceeds the outer diameter of the body of the first size syringe. The bottom wall of the second region of the second size cavity also includes an aperture disposed therein for receiving the distal tip of the body of the first size syringe.

Each third size cavity of the present tray defines a first, top region having an inner wall and an annular shoulder for supporting the body of the third size syringe. The inner wall of the first region of the third size cavity is of a third diameter which is substantially equal to but slightly exceeds the outer diameter of the body of the third size syringe. Each third size cavity further defines a second, middle region having an inner wall and an annular shoulder for supporting the body of the second size syringe. The inner wall of the second region of the third size cavity is of the second diameter which is substantially equal to but slightly exceeds the outer diameter of the body of the second size syringe. In addition to the first and second regions, each third size cavity defines a third, bottom region having inner and bottom walls for supporting the body of the first size syringe. The inner wall of the third region is of the first diameter which is substantially equal to but slightly exceeds the outer diameter of the body of the first size syringe. Additionally, the bottom wall of the third region includes an aperture disposed therein for receiving the distal tip of the body of the first size syringe.

In accordance with the present invention, the first size syringe typically comprises a 5 cc syringe, with the second size syringe comprising a 10 cc syringe and the third size syringe comprising a 20 cc syringe. Additionally, the first, second and third size cavities are preferably arranged in separate rows within respective ones of the first and second tiers, with the row of second size cavities being positioned between the rows of first and third size cavities. These rows are preferably formed within respective ones of the first and second tiers such that the second size cavities are laterally off-set relative to the first and third size cavities.

In the present tray, the third, lower tier is preferably devoid of syringe-receiving cavities wherein syringes may be inserted. Rather, the third tier is provided with a raised retaining lip extending peripherally thereabout such that articles may be independently placed upon and removed from the third tier. As such, the third tier includes a rectangularly configured, recessed well formed therein.

The tray constructed in accordance with the present invention, and more particularly the frame thereof, is preferably fabricated from a molded plastic material. The present tray may further comprise a sterility cover which is selectively attachable to the frame for covering the syringes held within the syringe-receiving cavities. In addition to the sterility cover, the tray may include a drip tray which is positionable beneath the frame for containing fluids which drip from the syringes held within the syringe-receiving cavities.

BRIEF DESCRIPTION OF THE DRAWINGS

FIG. 3 is a partial cross-sectional view through line 3—3 of FIG. 2, showing the manner in which the syringe-holding cavities of the apparatus are configured to accommodate differing sizes of syringes.

FIGS. 4a–4d show different sizes (e.g., 5 cc, 10 cc & 20 cc) syringes operatively positioned within the syringe-holding cavities of the preferred embodiment of the present invention as shown in FIGS. 1–3.

DETAILED DESCRIPTION OF THE PREFERRED EMBODIMENT

Figure 1:
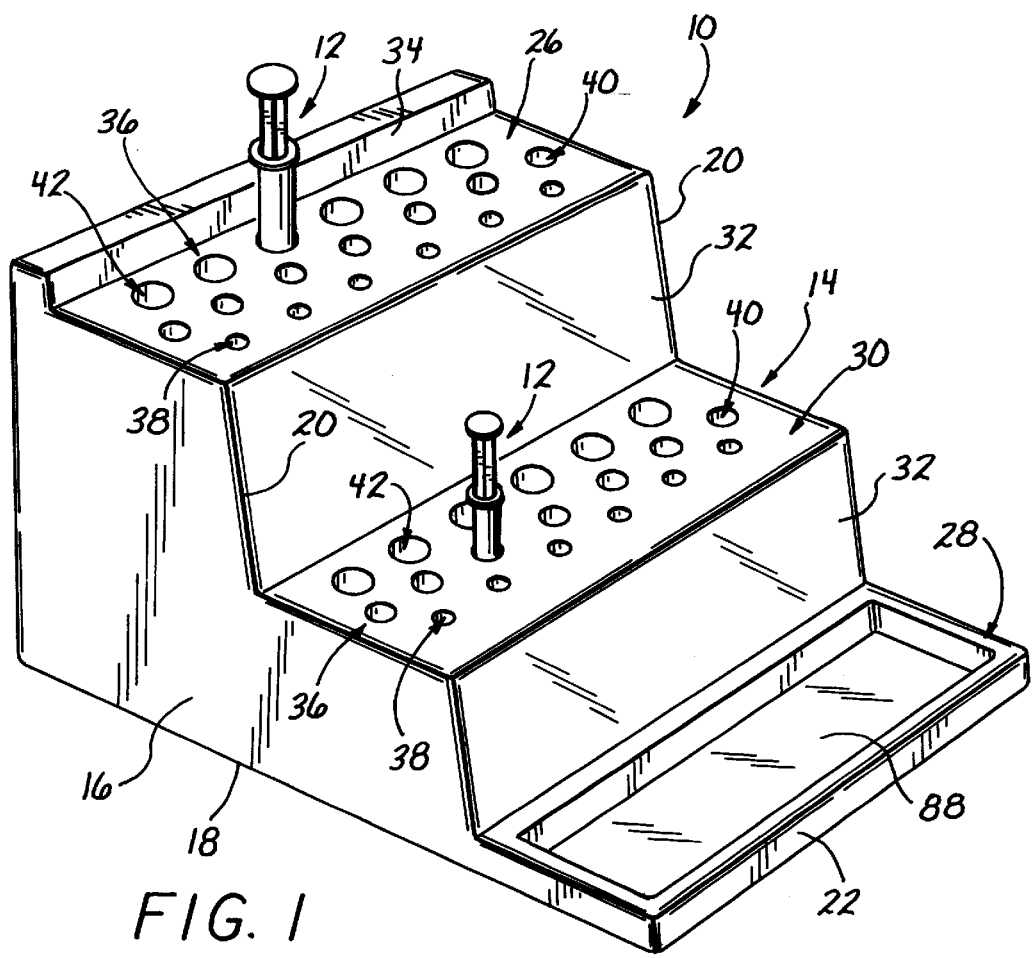
FIG. 1 is a perspective view of a preferred embodiment of a syringe-holding apparatus of the present invention.

Referring now to the drawings wherein the showings are for purposes of illustrating a preferred embodiment of the present invention only, and not for purposes of limiting the same, FIG. 1 perspectively illustrates the tray 10 of the present invention which is constructed to receive and hold a plurality of hypodermic syringes 12 of differing size. In the preferred embodiment, the tray 10 comprises a substantially rigid frame 14 which is preferably fabricated from a molded plastic material. The frame 14 is preferably hollow rather than being of solid construction. The frame 14 itself comprises an opposed pair of sidewalls 16, each of which defines a bottom edge 18 and a top edge 20 having a stepped configuration. In addition to the sidewalls 16, the frame 14 includes a front wall 22 and a back wall 24.

As further seen in FIG. 1, extending between the horizontally oriented sections of the stepped top edges 20 are three (3) upper walls, each of which has a generally rectangular configuration and defines a generally planar top surface. Due to the stepped configurations of the top edges 20, the three (3) upper walls are disposed at differing heights or elevations relative to each other. In this respect, the upper wall disposed at the highest elevation defines a first, upper tier 26 of the frame 14, with the upper wall disposed at the lowest elevation defining a third, lower tier 28 thereof. The upper wall which is disposed at an elevation intermediate those of the first and third tiers 26, 28 defines a second, middle tier 30 of the frame 14. Extending between the first and second tiers 26, 30 and between the second and third tiers 30, 28 are forwardly facing transitional walls 32. The transitional walls 32 do not extend perpendicularly relative to the bottom edges 18 of the sidewalls 16, but rather are slightly inclined. Additionally, extending along the back edge of the first tier 26 and extending upwardly therefrom is a ledge 34 which is partially defined by the back wall 24 of the frame 14.

Figure 2:
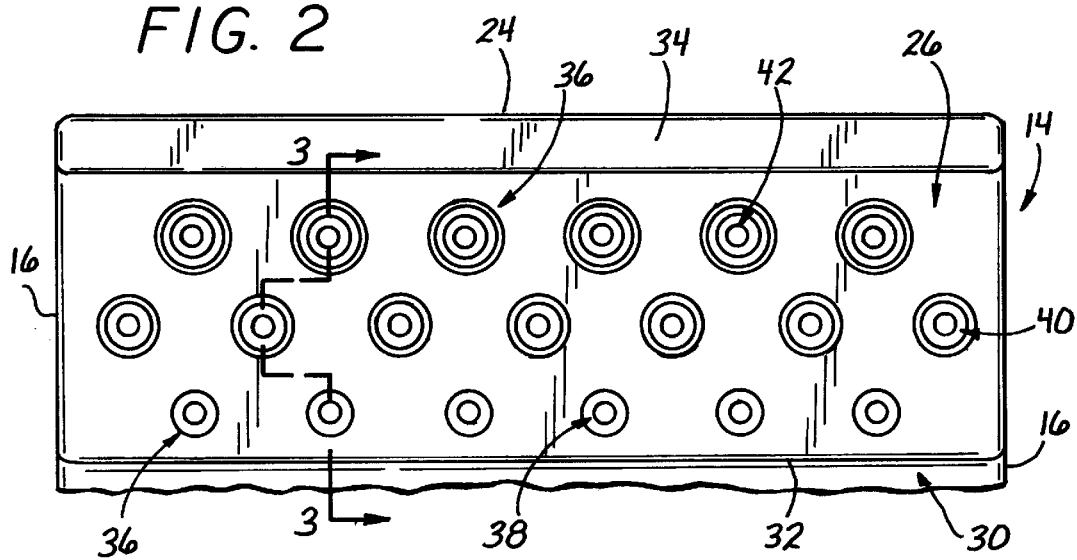
FIG. 2 is a top plan view of one tier of the preferred syringe-holding apparatus of FIG. 1.

Referring now to FIGS. 1–3, formed within the first and second tiers 26, 30, and more particularly the generally planar top surface defined thereby, are a plurality of syringe-receiving cavities 36. In the tray 10, each of the cavities 36 is sized and configured to receive and hold a syringe 12 in a generally vertical orientation. In the preferred embodiment, the cavities 36 formed within the first and second tiers 26, 30 are not all identically sized and configured. Rather, the first and second tiers 26, 30 each include first size cavities 38, second size cavities 40, and third size cavities 42 formed therein. As will be discussed in more detail below, each first size cavity 38 is adapted to receive and hold a first size syringe 12a which is typically a 5 cc syringe. Each second size cavity 40 is adapted to receive and hold either the first size syringe 12a or a second size syringe 12b which is typically a 10 cc syringe. Additionally, each third size cavity 42 is adapted to receive and hold either the first size syringe 12a, the second size syringe 12b, or a third size syringe 12c which is typically a 20 cc syringe. As seen in FIGS. 4a–4d, the syringes 12a, 12b, 12c each include a cylindrically configured, tubular body 44a, 44b, 44c which defines a reduced diameter distal tip 46a, 46b, 46c.

Referring now to FIGS. 3 and 4a–4d, the first size cavities 38 of the tray 10 each define an inner wall 48 and a bottom wall 50 which collectively support the body 44a of the first size syringe 12a. In this respect, the inner wall 48 is of a first diameter which is substantially equal to, but slightly exceeds, the outer diameter of the body 44a. Disposed within the bottom wall 50 is an aperture 52 for receiving, i.e., accommodating, the distal tip 46a of the body 44a in the manner shown in FIG. 4d.

Each second size cavity 40 of the tray 10 includes a first, top region 54 having an inner wall 56 and an annular shoulder 58 which collectively support the body 44d of the second size syringe 12b. In this respect, the inner wall 56 is of a second diameter which is substantially equal to, but slightly exceeds, the outer diameter of the body 44b. In addition to the first region 54, each second size cavity 40 includes a second, bottom region 60 having an inner wall 62 and a bottom wall 64 which collectively support the body 44a of the first size syringe 12a. In this respect, the inner wall 62 of the second region 60 is of the same first diameter as the inner wall 48 of the first size cavity 38 for accommodating the body 44a of the first size syringe 12a. Additionally, the bottom wall 64 of the second region 60 is identically configured to the bottom wall 50 of the first size cavity 38, with an aperture 66 being disposed within the bottom wall 64 for receiving the distal tip 46a of the body 44a.

Each third size cavity 42 of the tray 10 includes a first, top region 68 having an inner wall 70 and an annular shoulder 72 which collectively support the body 44c of the third size syringe 12c. In this respect, the inner wall 70 of the first region 68 is of a third diameter which is substantially equal to, but slightly exceeds, the outer diameter of the body 44c. Each third size cavity 42 further includes a second, middle region 74 having an inner wall 76 and a shoulder 78 which collectively support the body 44b of the second size syringe 12b. In this respect, the inner wall 76 of the second region 74 is of the same second diameter as the inner wall 56 of the first region 54 of the second size cavity 40 for properly accommodating the body 44b of the second size syringe 12b. Additionally, the shoulder 78 of the second region 74 is identically configured to the shoulder 58 of the first region 54 of the second size cavity 40.

In addition to the first and second regions 68, 74, each third size cavity 42 includes a third, lower region 80 having an inner wall 82 and a bottom wall 84 which collectively support the body 44a of the first size syringe 12a. In this respect, the inner wall 82 of the third region 80 is of the same first diameter as are the inner walls 62, 48 of the second and first size cavities 40, 38 for properly accommodating the body 44a of the first size syringe 12a. Additionally, the bottom wall 84 is identically configured to the bottom walls 64, 50 of the second and first size cavities 40, 38, with an aperture 86 being disposed within the bottom wall 84 for receiving the distal tip 46a of the body 44a.

As is evident from the foregoing description of the first, second and third size cavities 38, 40, 42, each first size cavity 38 is adapted to receive and hold only the first size syringe 12a. Each second size cavity 40 is adapted to receive and hold either the first size syringe 12a (which is supported by the second region 60) or the second size syringe 12b (which is supported by the first region 54). Each third size cavity 42 is adapted to receive and hold either the first size syringe 12a (which is supported by the third region 80 as seen in FIG. 4c), the second size syringe 12b (which is supported by the second region 74 as shown in FIG. 4b), or the third size syringe 12c (which is supported by the first region 68 as shown in FIG. 4a).

In the preferred embodiment of the present invention, the first and second tiers 26, 30 each include six (6) first size cavities 38, seven (7) second size cavities 40, and six (6) third size cavities 42 formed therein. The first, second and third size cavities 38, 40, 42 are not randomly distributed within respective ones of the first and second tiers 26, 30, but rather are arranged in three (3) separate rows therewithin. More particularly, the first and second tiers 26, 30 are each provided with a row of the first size cavities 38 which is disposed closest to the front edge thereof, and a row of the third size cavities 42 which is disposed closest to the back edge thereof. Disposed between the rows of first and third size cavities 38, 42 within each tier 26, 30 is a row of the second size cavities 40. As best seen in FIG. 2, the second size cavities 40 of each intermediate row thereof are not centrally positioned between respective pairs of the first and third size cavities 38, 42, but rather are laterally off-set relative thereto. Such off-set allows an extra second size cavity 40 to be included in each row thereof. Those of ordinary skill in the art will recognize that the tray 10 may be formed to include greater or fewer members of each of the different size cavities 36, 38, 40 in any one of a wide variety of different orientations within the first and second tiers 26, 30.

As best seen in FIG. 1, the third, lower tier 28 of the frame 14 does not include any syringe-receiving cavities 36 formed therewithin. Rather, formed within the generally planar top surface defined by the third tier 28 is a rectangularly configured, recessed well 88. The well 88 is adapted to accommodate articles which may be independently placed upon and removed from the third tier 28.

Figure 5:
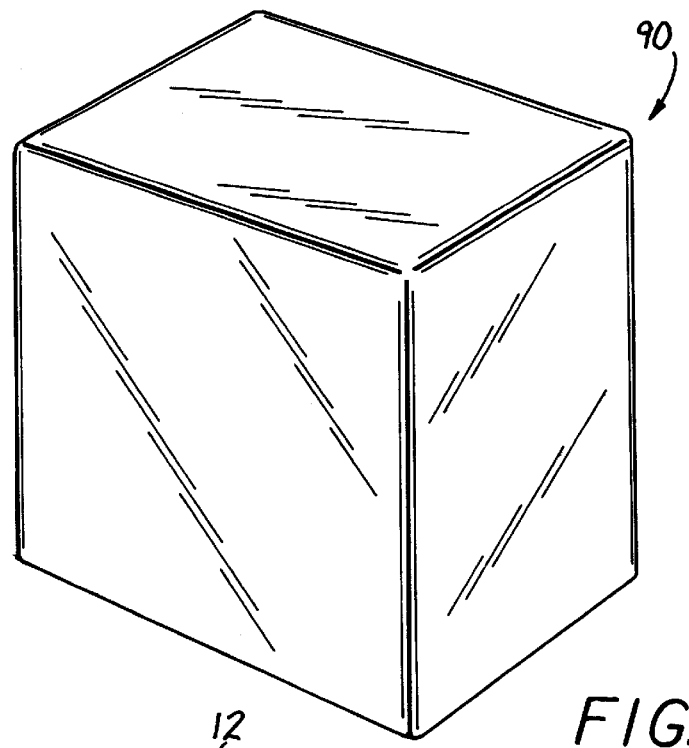
FIG. 5 is an exploded view showing a sterility cover and drip tray which may be used with the preferred embodiment of the present invention as shown in FIG. 1.
Figure 5:
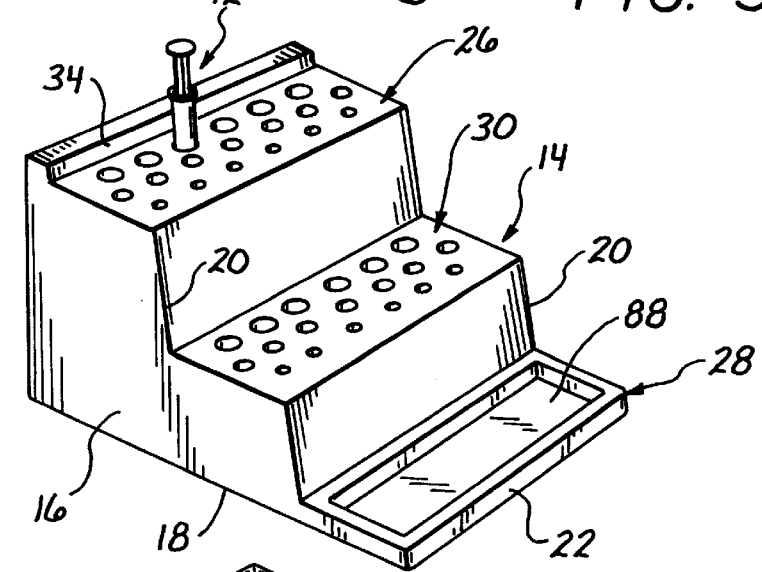
Figure 5:
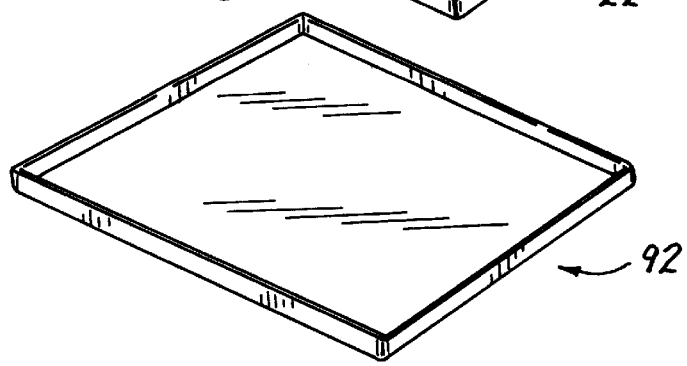

Referring now to FIG. 5, the tray 10 of the present invention may further comprise a sterility cover 90 which is selectively extensible over and attachable to the frame 14 for covering the syringes 12 held within the syringe-receiving cavities 36. Additionally, the tray 10 may comprise a drip tray 92 which is selectively positionable beneath the frame 14 for containing fluids which drip from the syringes 12 held within the syringe-receiving cavities 36.

Additional modifications and improvements of the present invention may also be apparent to those of ordinary skill in the art. Thus, the particular combination of parts described and illustrated herein is intended to represent only one embodiment of the present invention, and is not intended to serve as limitations as alternative devices within the spirit and scope of the invention.

What is claimed is:

1. An article of manufacture which is constructed to receive and hold a plurality of syringes of differing size, said article comprising:

a substantially rigid frame having a plurality of tiers formed thereon, each of said teirs having a top surface;

a plurality of syringe-receiving cavities formed in at least one of the tiers, each of said syringe-receiving cavities being sized and configured to receive and hold a syringe in a generally vertical orientation;

at least some of said syringe-receiving cavities being variable diameter syringe-receiving cavities, which are adapted to receive different sizes of syringes, each of said variable diameter syringe-receiving cavities having an inner surface which defines:

i) a first region having an inner wall of a first diameter to receive and hold a syringe which has an outer diameter substantially equal to said first diameter; and ii) a second region having an inner wall of a second diameter to receive and hold a syringe which has an outer diameter substantially equal to said second diameter.

2. The article of claim 1 wherein said article comprises:

a first, upper tier;

a second, middle tier; and, a third, lower tier.

3. The article of claim 1 wherein said upper, middle, and lower tiers being disposed at different elevations relative to each other, with the top surfaces of at least said upper and middle tiers having said syringe-receiving cavities formed therein.

4. The article of claim 2 wherein the top surface of the third, lower tier has at least one indentation formed therein such that excess syringes may be placed within such indentation in a generally horizontal orientation.

5. The article of claim 1 wherein said syringe-receiving cavities include:

at least one of said syringe cavities of a first size for receiving and holding a syringe of a first size; and, at least one of said syringe-receiving cavities is of a second size, for receiving and holding a syringe of a second size.

6. The article of claim 5 wherein said syringe-receiving cavities further include:

at least one of said syringe-receiving cavities of a third size, for receiving syringes of a third size.

7. The article of claim 1 wherein said syringe-receiving cavities comprise:

cylindrical cavities having a cylindrical side wall which emanates upwardly from a generally horizontal floor; and, a central aperture formed in the floor of each cavity, such that a syringe having a cylindrical side wall and a Luer tip extending distally therefrom may be inserted downwardly into aperture with the side wall of the syringe in abutment against the cylindrical side wall of the cavity and the Luer tip of the syringe extending through the aperture formed in the floor of the cavity.

8. The article of claim 1 wherein said syringe-receiving cavities are sized to receive and hold syringes of 5 cc, 10 cc and 20 cc size.

9. The article of claim 1 further comprising:

a sterility-maintaining cover mountable on said frame attached to prevent contamination of syringes inserted within the syringe-receiving cavities.

10. The article of claim 7 wherein article further comprises:

a drip tray positioned beneath the apertures formed in the floors of the syringe-receiving cavities such that any liquid which drips from syringes inserted into such cavities will be received and contained within said drip tray.

* * * * *